(12) United States Patent
Roberts et al.

(10) Patent No.: US 6,232,272 B1
(45) Date of Patent: May 15, 2001

(54) MANUFACTURE AND USE OF HERBICIDE CHLORINATED PHENOXY FORMULATION

(75) Inventors: Johnnie R. Roberts, Memphis; Greg Volgas, Bartlett, both of TN (US)

(73) Assignee: Helena Chemical Company, Memphis, TN (US)

( * ) Notice: Subject to any disclaimer, the term of this patent is extended or adjusted under 35 U.S.C. 154(b) by 0 days.

(21) Appl. No.: 09/261,522

(22) Filed: Mar. 3, 1999

Related U.S. Application Data

(60) Provisional application No. 60/118,254, filed on Feb. 2, 1999.

(51) Int. Cl.[7] .............................. A01N 25/30; A01N 39/02
(52) U.S. Cl. ............................................. 504/323; 504/362
(58) Field of Search ....................................... 504/323, 362

(56) References Cited

U.S. PATENT DOCUMENTS

| | | | |
|---|---|---|---|
| 5,561,099 | * 10/1996 | Murphy et al. | 504/116 |
| 5,580,567 | * 12/1996 | Roberts | 424/405 |

* cited by examiner

*Primary Examiner*—S. Mark Clardy
(74) *Attorney, Agent, or Firm*—Connolly, Bove, Lodge & Hutz LLP

(57) ABSTRACT

The invention pertains to a method for increasing the activity of chlorinated phenoxy herbicides by specially formulating said herbicides with a combination of solvent and selected surfactants. This method requires the use of alkylated fatty esters and can also include organosilicone surfactants. This unique combination of components has been seen to allow lower use rates of chlorinated phenoxy herbicides.

22 Claims, No Drawings

MANUFACTURE AND USE OF HERBICIDE CHLORINATED PHENOXY FORMULATION

This application claims priority to U.S. Provisional Application Ser. No. 60/118,254, filed Feb. 2, 1999.

BACKGROUND OF THE INVENTION

As early as 1988, Henkel Corporation began marketing a line of methylated fatty acids, and more specifically, methylated soybean oil, as a replacement for commonly used organic solvents used in pesticide formulations. These methyl esters were and still are, promoted as being safer solvents because of their high flash point, relative to more commonly used aromatic hydrocarbons. In 1986, F. A. Manthey, et. Al., published a paper showing their work on various alkylated esters of different natural oils (soybean and sunflower). This work demonstrated that alkylated esters of soybean oil and sunflower oil can enhance the uptake of oxime herbicides (commonly referred to as "dims" or graminicides, i.e. sethoxydim, clopropoxydim.), and 2-(4-aryloxyphenoxy)alkanoic acid herbicides (commonly known as "fops", i.e. diclofop, quizalofop, fluazifop). In 1989, Hazen, et.al. demonstrated the effectiveness of a methylated sunflower oil adjuvant on the uptake of sethoxydim. Furthermore, it was reported that methylated sunflower oil could actually increase the stability of sethoxydim in direct sunlight. Also in 1989, Manthey, et.al. reported that alkylated vegetable oils such as soybean oil and sunflower oil, could increase the realtive wax solubility of pesticide sprays. In 1991, more work was done by Urvoy, et Al. That demonstrated the effectiveness of alkylated fatty acids in enhancing the uptake of gramincides. In 1993, Serre, et.al. reported that alkyl esters of oleic acid could enhance the efficacy of quizalofop-ethyl, a 2-(4-aryloxyphenoxy)alkanoic acid herbicide, and phenmedipham, a bis-carbamate herbicide. In 1995, McMullan, et.al. demonstrated the effectiveness of methylated fatty acids in enhancing the efficacy of tralkoxydim, another graminicide herbicide.

Chlorinated phenoxy acid compounds comprise a family of herbicides that are used in the form of their parent acids, and more commonly as their salts and esters. The most common member of this herbicide family is 2,4-D [(2,4-dichlorophenoxy)acetic acid]. Two other commonly used compounds in this family are 2,4,5-T [(2,4,5-trichlorophenoxy)acetic acid] and MCPA[[(4-chloro-o-tolyl)oxy]acetic acid]. Additional herbicides in this family are 2,4-DB [4(2,4-dichlorophenoxy)butyric acid], MCPB [4-[(4-chloro-o-tolyl)oxy]butyric acid], silvex [2-(2,4,5-trichorophenoxy)propionic acid], dichlorprop [2-(2,4-dichlorophenoxy)propionic acid], mercoprop [2-[(4-chloro-o-tolyl)oxy]propionic acid]. These herbicides are plant growth regulator compounds with hormone-like activity.

The ester forms of these compounds are represented by the alkyl esters (mainly methyl, isopropyl, butyl, and octyl) and the low-volatile esters (butoxyethanol, propyleneglycolbutylether, and iso-octyl).

The major controllable factors of chlorinated phenoxy herbicides have been reported by Ashton and Crafts as being pH, concentration, and additives (i.e. surfactants). Absorption of chlorinated phenoxy herbicides is reported to be optimal at low pH ranges. While surfactants have been reported to enhance the activity of chlorinated phenoxy herbicides in some instances, no one surfactant could be selected which consistently enhanced the uptake of the herbicide. The authors cite work done by Bukovac in 1976 showing that foliar penetration is generally linearly related to the external herbicide concentration.

Recently, the family of 2,4-D herbicides has come under regulatory scrutiny due to the potential of spray mixes to drift to off-target areas. This drift is caused by volatilization of both sprays and of spray deposits. Therefore, it would be beneficial if the per acre use rate of these compounds could be reduced, thereby affording a reduction in driftable herbicide. Any attempt to reduce herbicide drift, however, must not demonstrate a reduction in herbicide efficacy.

SUMMARY OF THE INVENTION

The present invention is a homogenous agricultural liquid composition containing at least one chlorinated phenoxy herbicide and at least one alkylated fatty acid or natural oil, and optionally, at least one organosilicone surfactant. Such formulations have been seen to exhibit synergistic effects allowing a reduction of herbicide use rates on a per acre basis.

DETAILED DESCRIPTION OF THE NEW INVENTION

It has been surprisingly discovered that a chlorinated phenoxy herbicides can be formulated with alkylated fatty acids or natural oils, and that the effective use rate of the composition can be reduced dramatically. This is in opposition to prior knowledge that the uptake of chlorinated phenoxy herbicides is directly associated with the concentration of the herbicide on the plant leaf surface.

In example 1, the following formulations were tested:

The control formulation:

| Ingredients | % in formula |
| --- | --- |
| Iso-octyl ester of 2,4-D | 83.10 |
| Aromatic 100 | 11.90 |
| Sponto N-702/710 | 5.00 |

The new formulation listed as HM-9625-B

| Iso-octyl ester of 2,4-D | 83.10 |
| --- | --- |
| Methylated soybean oil | 9.90 |
| Silwet L-77 | 2.00 |
| Sponto N-702/710 | 5.00 |

Aromatic 100 is a conventional organic solvent containing aromatic hydrocarbons and is sold by Exxon.

Sponto N-702/710 is a mixed emulsifier specially blended by Witco Corp. to provide stable emulsions of 2,4-D ester formulations.

Methylated soybean oil is a methylated natural oil derived from soybean oil. It is manufactured by several US producers by the reaction of methanol and soybean oil.

Silwet L-77 is an organosilicone surfactant manufactured by Witco Corp. It is generally used to enhance the spreadability of water based sprays. Silwet L-77 has also been reported to enhance the uptake of herbicides through stomatal infiltration.

In the chart below, HM-8802-A is a commercially available adjuvant containing methylated soybean oil and Silwet L-77.

| | Control of Giant Ragweed | |
|---|---|---|
| Treatment | 7 days after treatment | 14 days after treatment |
| Control at 7 ounces per acre | 56.3% | 71.3% |
| Control at 7 ounces per acre plus HM-8802-A at 0.5% v/v | 60.0% | 66.3% |
| HM-9625-B at 7 ounces per acre | 62.5% | 70.0% |
| HM-9625-B at 4.5 ounces per acre | 65.0% | 67.5% |

The improvement of this formula was originally thought to be simply the increased flash point and thus enhanced product safety. The flash point went from about 100 degrees F. using Aromatic 100, to over 200 degrees F. using the methylated soybean oil. While this benefit is certainly useful, it is hardly suprising or original. Henkel has been touting their methyl esters for this characteristic for several years. We were surprised to discover that this formula provided herbicidal efficacy at low use rates. The data table above shows better weed control as compared to the control formulation at higher rates. Furthermore, it was discovered that the formulation containing methylated soybean oil and organosilicone surfactant was superior to the addition of a methylated soybean oil/organosilicone surfactant adjuvant to the control formulation.

In example 2, the same materials were tested for herbicide efficacy on a separate weed species, common lambsquarter.

| | Control of Common Lambsquarter | |
|---|---|---|
| Treatment | 7 days after treatment | 14 days after treatment |
| Control at 7 ounces per acre | 50% | 69% |
| Control at 7 ounces per acre plus HM-8802-A at 0.5% v/v | 50% | 80% |
| HM-9625-B at 7 ounces per acre | 50% | 73% |
| HM-9625-B at 4.5 ounces per acre | 50% | 78% |

The data table above shows equivalent weed control as compared to the control formulation at higher rates. Furthermore, it was discovered that the formulation containing methylated soybean oil and organosilicone surfactant was equal to the addition of a methylated soybean oil/organosilicone surfactant adjuvant to the control formulation. This is significant because lower herbicide use rates are more environmentally friendly. Also, these findings with the improved formulation are different from what was previously believed, that concentration was the largest single factor involved in chlorinated phenoxy herbicide uptake.

In example 3, the novel formulation is shown using ethylated sunflower oil as the alkylated fatty acid. Ethylated sunflower oil is made by reacting natural sunflower oil with ethyl alcohol.

| | |
|---|---|
| Iso-octyl ester of 2,4-D | 83.10 |
| Ethylated sunflower oil | 9.90 |
| Silwet L-77 | 2.00 |
| Sponto N-702/710 | 5.00 |

In example 4, the chlorinated phenoxy herbicide of choice is MCPA, or specifically, the iso-octyl ester of MCPA.

| | |
|---|---|
| Iso-octyl ester of MCPA | 83.10 |
| Methylated soybean oil | 9.90 |
| Silwet L-77 | 2.00 |
| Sponto N-702/710 | 5.00 |

In example 5, the formula contains a nonylphenol ethoxylate surfactant in place of the organosilicone surfactant

| | |
|---|---|
| Iso-octyl ester of 2,4-D | 83.10 |
| Methylated soybean oil | 9.90 |
| 6-mole nonylphenol ethoxylate | 2.00 |
| Sponto N-702/710 | 5.00 |

The preferred embodiment of the present invention includes chlorinated phenoxy herbicides. The most preferred embodiment of the present invention includes 2,4-dichlorophenoxyacetic acid and its' iso-octyl ester.

The preferred embodiment of the present invention includes alkylated fatty acids or natural oils, including but not limited to the following:

Alkylated soybean oil

Alkylated sunflower oil

Alkylated canola oil

Alkylated fatty acids including $C_{6-18}$ saturated and unsaturated fatty acids.

The preferred embodiment of the present invention includes additional surfactants to enhance the spreading characteristics of the spray deposit. These surfactants preferably include those listed in the prior patents U.S. Pat. No. 5,393,791 and U.S. Pat. No. 5,580,567 which are incorporated by reference herein. The most preferred embodiment of the present invention includes organosilicone surfactants.

What is claimed is:

1. A composition which comprises (a) at least one chlorinated phenoxy herbicide, (b) at least one alkylated fatty acid, alkylated plant derived oil or alkylated animal derived oil, and (c) at least one surfactant.

2. The composition group as claimed in claim 1, wherein said chlorinated phenoxy herbicide is in the acid, ester or salt form and at least one of said chlorinated phenoxy herbicide is selected from the group consisting of: 2,4-D{(2,4-dichlorophenoxy)acetic acid}, 2,4,5-T {(2,4,5-trichlorophenoxy)acetic acid}, MCPA {{(4-chloro-o-tolyl)oxy}acetic acid}, 2,4-DB {4(2,4-dichlorophenoxy)butyric acid}, MCPB {4-{4-chloro-o-tolyl)}butyric acid}, silvex {2-(2,4,5-trichlorophenoxy)propionic acid}, dichlorprop{2-(2,4-dichlorophenoxy) propionic acid}, and mercoprop {2-{4-chloro-o-tolyl)oxy}propionic acid}.

3. The composition as claimed in claim 1, wherein at least one alkylated fatty acid is present and at least one alkylated fatty acid is selected from the group consisting of:

methyl oleate, ethyl oleate, methyl linoleate, ethyl linoleate, methyl laurate, ethyl laurate, methyl palmitate, ethyl palmitate, methyl stearate and ethyl stearate.

4. The composition as claimed in claim 2, wherein at least one alkylated fatty acid is present and at least one alkylated fatty acid is selected from the group consisting of:

methyl oleate, ethyl oleate, methyl linoleate, ethyl linoleate, methyl laurate, ethyl laurate, methyl palmitate, ethyl palmitate, methyl stearate and ethyl stearate.

5. The composition as claimed in claim 1, wherein said alkylated plant derived oil is presented and at least one alkylated plant derived oil is selected from the group consisting of:

a) methylated or ethylated soybean oil, b) methylated or ethylated canola oil, c) methylated or ethylated sunflower oil and d) methylated or ethylated coconut oil.

6. The composition as claimed in claim 2, wherein said alkylated plant derived oil is presented and at least one alkylated plant derived oil is selected from the group consisting of:

d) methylated or ethylated soybean oil, e) methylated or ethylated canola oil, c) methylated or ethylated sunflower oil and d) methylated or ethylated coconut oil.

7. The composition as claimed in claim 1, wherein at least one surfactant is selected from the group consisting of:

a) sorbitan fatty acids, b) sorbitan fatty acid esters, c) ethoxylated sorbitan fatty acid esters d) propoxylated fatty acid esters, e) silicone surfactants of the formulas (I), (II) or (III)

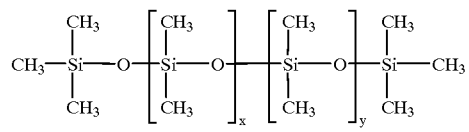

(I)

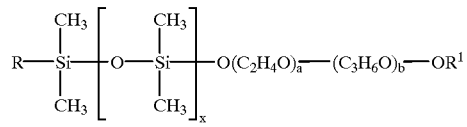

(II)

or

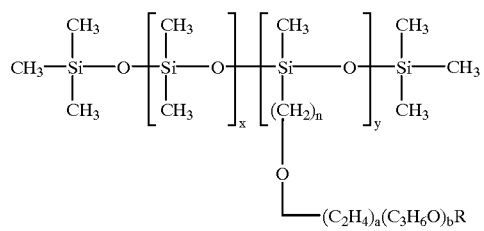

(III)

wherein X and Y independently of one another are from 1 to 100, R and $R^1$ independently from one another are hydrogen, alkyl having from 1 to about 20 carbon atoms, or an alkyl ester group having 1 to 20 carbon atoms, a is a number from about 3 to about 25, b is a number from about 0 to about 25, n is a number from about 2 to about 4, f) ethoxylated fatty acids, g) branched and linear alkyl ethoxylates and phosphate or carboxylate acid esters thereof, h) alkylphenol ethoxylates and phosphate or carboxylate acid esters thereof, i) polypropylene glycols, j) polyethylene glycols, k) block copolymers of ethylene oxide and propylene oxide and phosphate or carboxylate acid esters thereof l) fatty alkanolamides of the formula

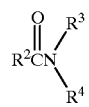

wherein $R^2$ is an alkyl group having about 6 to about 25 carbon atoms; $R^3$ and $R^4$ independently of one another are selected from the group consisting of hydrogen,

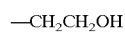

—$CH_2CH_2OH$ and

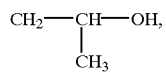

m) peg esters of the formula

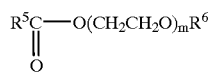

wherein $R^5$ is a fatty alkyl having from about 2 to about 25 carbon atoms, $R^6$ is a fatty alkyl having from about 2 to about 25 carbon atoms or H and m is a number from 1 to about 100, n) tristyrylphenol alkoxylates, o) amine ethoxylates, p) n-acyl sarcosines or sodium n-acyl sarcosinates, q) alkylaryl polyethoxy phosphate ester, r) alkylaryl polyethoxy carboxylate ester, s) tristyrylphenol alkoxylate phosphate esters, t) tristyrylphenol alkoxylate carboxylate esters, u) phosphate esters of block copolymers of ethylene and propylene oxide and v) alkylpolyglucosides.

8. The composition as claimed in claim 4, wherein at least one surfactant is selected from the group consisting of:

a) sorbitan fatty acids, b) sorbitan fatty acid esters, c) ethoxylated sorbitan fatty acid esters d) propoxylated fatty acid esters, e) silicone surfactants of the formulas (I), (II) or (III)

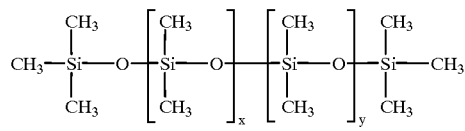
(I)

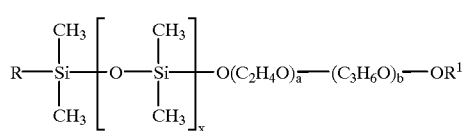
(II)

or

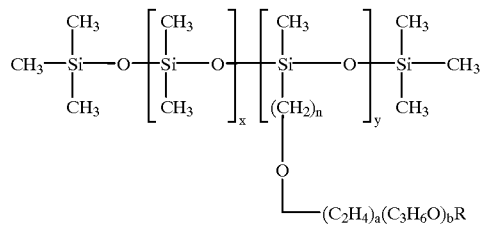
(III)

wherein X and Y independently of one another are from 1 to 100, R and $R^1$ independently from one another are hydrogen, alkyl having from 1 to about 20 carbon atoms, or an alkyl ester having 1 to 20 carbon atoms, a is a number from about 3 to about 25, b is a number from about 0 to about 25, n is a number from about 2 to about 4, f) ethoxylated fatty acids, g) branched and linear alkyl ethoxylates and phosphate or carboxylate acid esters thereof, h) alkylphenol ethoxylates and phosphate or carboxylate acid esters thereof, i) polypropylene glycols, j) polyethylene glycols, k) block copolymers of ethylene oxide and propylene oxide and phosphate or carboxylate acid esters thereof l) fatty alkanolamides of the formula

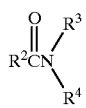

wherein $R^2$ is an alkyl group having about 6 to about 25 carbon atoms; $R^3$ and $R^4$ independently of one another are selected from the group consisting of hydrogen,

and

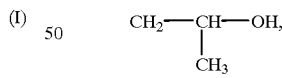

m) peg esters of the formula

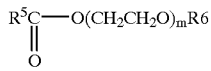

wherein $R^5$ is a fatty alkyl having from about 2 to about 25 carbon atoms, $R^6$ is a fatty alkyl having from about 2 to about 25 carbon atoms or H and m is a number from 1 to about 100, n) tristyrylphenol alkoxylates, o) amine ethoxylates, p) n-acyl sarcosines or sodium n-acyl sarcosinates, q) alkylaryl polyethoxy phosphate ester, r) alkylaryl polyethoxy carboxylate ester, s) tristyrylphenol alkoxylate phosphate esters, t) tristyrylphenol alkoxylate carboxylate esters, u) phosphate esters of block copolymers of ethylene and propylene oxide and v) alkylpolyglucosides.

9. The composition as claimed in claim 6, wherein at least one surfactant is selected from the group consisting of:

a) sorbitan fatty acids, b) sorbitan fatty acid esters, c) ethoxylated sorbitan fatty acid esters d) propoxylated fatty acid esters, e) silicone surfactants of the formulas (I), (II) or (III)

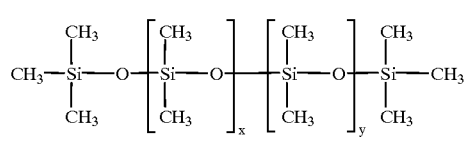
(I)

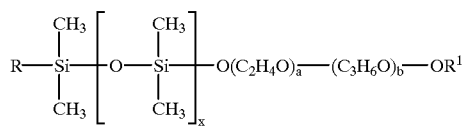
(II)

or

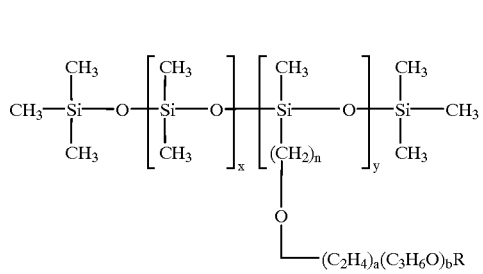
(III)

wherein X and Y independently of one another are from 1 to 100, R and $R^1$ independently from one another are hydrogen, alkyl having from 1 to about 20 carbon atoms, or an alkyl ester group having 1 to 20 carbon atoms, a is a number from about 3 to about 25, b is a number from about 0 to about 25, n is a number from about 2 to about 4, f) ethoxylated fatty acids, g) branched and linear alkyl ethoxylates and phosphate or carboxylate acid esters thereof, h) alkylphenol ethoxylates and phosphate or carboxylate acid esters thereof, i) polypropylene glycols, j) polyethylene glycols, k) block copolymers of ethylene oxide and propylene oxide and phosphate or carboxylate acid esters thereof l) fatty alkanolamides of the formula

wherein $R^2$ is an alkyl group having about 6 to about 25 carbon atoms; $R^3$ and $R^4$ independently of one another are selected from the group consisting of hydrogen,

and

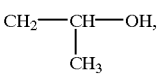

m) peg esters of the formula

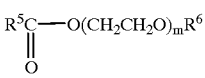

wherein $R^5$ is a fatty alkyl having from about 2 to about 25 carbon atoms, $R^6$ is a fatty alkyl having from about 2 to about 25 carbon atoms or H and m is a number from 1 to about 100, n) tristyrylphenol alkoxylates, o) amine ethoxylates, p) n-acyl sarcosines or sodium n-acyl sarcosinates, q) alkylaryl polyethoxy phosphate ester, r) alkylaryl polyethoxy carboxylate ester, s) tristyrylphenol alkoxylate phosphate esters, t) tristyrylphenol alkoxylate carboxylate esters, u) phosphate esters of block copolymers of ethylene and propylene oxide and v) alkylpolyglucosides.

10. The composition as claimed in claim 1, which further comprises at least one organosilicone surfactant in addition to said at least one surfactant.

11. The composition as claimed in claim 2, which further comprises at least one organosilicone surfactant in addition to said at least one surfactant.

12. The composition as claimed in claim 3, which further comprises at least one organosilicone surfactant in addition to said at least one surfactant.

13. The composition as claimed in claim 5, which further comprises at least one organosilicone surfactant in addition to said at least one surfactant.

14. The composition as claimed in claim 7, which further comprises at least one organosilicone surfactant in addition to said at least one surfactant.

15. The composition as claimed in claim 7, wherein at least one surfactant is selected from the group consisting of:

a) ethoxylated fatty acids of the following formula

wherein $R^7$ is an alkyl group having from about 6 to about 25 carbon atoms, n is a number from 1 to about 100, b) alkyl ethoxylates of the following formula

wherein $R^8$ is an alkyl group having from about 1 to about 50 carbon atoms and x is a number from 1 to 100, c) alkylphenol ethoxylates of the following formula

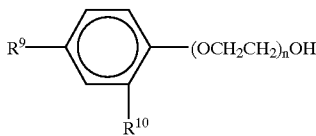

wherein $R^9$ is H or an alkyl having from about 1 to about 20 carbons, $R^{10}$ is H or an alkyl having from about 1 to about 20 carbons and n is a number from 1 to about 100, d) polypropylene glycols of the following formula

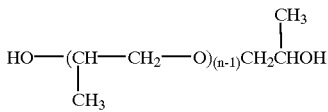

wherein n is a number from 1 to about 100 and e) amine ethoxylates of the following formula,

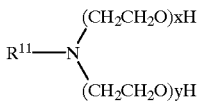

wherein x and y independently of one another are a number from about 1 to about 100 and $R^{11}$ is an alkyl having from 1 to about 25 carbon atoms.

16. A composition which comprises:
(A) at least one chlorinated phenoxy herbicide, and
(B) at least one an alkylated fatty acid, an alkylated plant derived oil or an alkylated animal derived oil.

17. The composition as claimed in claim 16, wherein said chlorinated phenoxy herbicide is in the acid, ester or salt form and at least one of said chlorinated phenoxy herbicide is selected from the group consisting of: 2,4-D{(2,4-dichlorophenoxy)acetic acid}, 2,4,5-T {(2,4,5-trichlorophenoxy)acetic acid}, MCPA {{(4-chloro-o-tolyl)oxy}acetic acid}, 2,4-DB {4(2,4-dichlorophenoxy)butyric acid}, MCPB {4-{4-chloro-o-tolyl}}butyric acid}, silvex {2-(2,4,5-trichlorophenoxy)propionic acid}, dichlorprop {2-(2,4-dichlorophenoxy)propionic acid}, and mecoprop {2-{4-chloro-o-tolyl)oxy}propionic acid}.

18. The composition as claimed in claim 16, wherein at least one alkylated fatty acid is present and at least one alkylated fatty acid is selected from the group consisting of: methyl oleate, ethyl oleate, methyl linoleate, ethyl linoleate, methyl laurate, ethyl laurate, methyl palmitate, ethyl palmitate, methyl stearate and ethyl stearate.

19. The composition as claimed in claim 16, wherein said alkylated plant derived oil is presented and at least one alkylated plant derived oil is selected from the group consisting of:
a) methylated or ethylated soybean oil,
b) methylated or ethylated canola oil,
c) methylated or ethylated sunflower oil and
d) methylated or ethylated coconut oil.

20. The composition as claimed in claim 1, which comprise an ester form of 2,4-dichlorophenoxyacetic acid, methylated soybean oil and an organosilicone surfactant.

21. The composition as claimed in claim 7, wherein a silicon surfactant of formula III is present and $R^1$ and R' independently from one another are hydrogen, alkyl having from 1 to 4 carbon atoms or an alkyl ester group having 1 to 4 carbon atoms, x is a number from about 1 to about 5, a is a number from about 3 to about 25, b is a number from about 0 to about 25, n is a number from about 2 to about 4.

22. A composition which comprises
(a) at least one chlorinated phenoxy herbicide,
(b) at least one alkylated fatty acid, alkylated plant derived oil or alkylated animal derived oil, and
(c) at least one surfactant selected from the group consisting of
1) sorbitan fatty acids
2) sorbitan fatty acid esters
3) ethoxylated sorbitan fatty acid esters
4) propoxylated fatty acid esters,
5) silicone surfactants of the formulas (II) or (III)

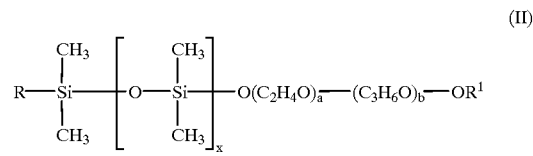

or

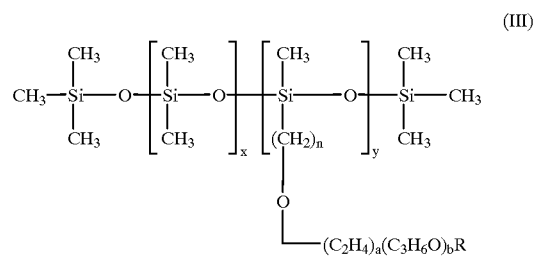

wherein X and Y are independently of one another are from 1 to 100, R and $R^1$ independently from one another are hydrogen, alkyl having from 1 to about 20 carbon atoms, or an alkyl ester group having 1 to 20 carbon atoms, a is a number from about 3 to about 25, b is a number from about 0 to about 25, n is a number from about 2 to about 4, 6) ethoxylated fatty acids,
7) branched and linear alkyl ethoxylates and phosphate or carboxylate acid esters thereof,
8) alkylphenol ethoxylates and phosphate or carboxylate acid esters thereof,
9) polypropylene glycols,
10) polyethylene glycols,
11) block copolymers of ethylene oxide and propylene oxide and phosphate or carboxylate acid esters thereof
12) fatty alkanolamides of the formula

wherein $R^2$ is an alkyl group having about 6 to about 25 carbon atoms; $R^3$ and $R^4$ independently of one another are selected from the group consisting of hydrogen,

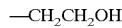

and

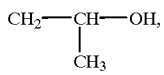

13) peg esters of the formula

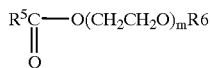

wherein $R^5$ is a fatty alkyl having from about 2 to about 25 carbon atoms, $R^6$ is a fatty alkyl having from about 2 to about 25 carbon atoms or H and m is a number from 1 to about 100,
14) tristyrylphenol alkoxylates,
15) amine ethoxylates,
16) n-acyl sarcosines or sodium n-acyl sarcosinates,
17) alkylaryl polyethoxy phosphate ester,
18) alkylaryl polyethoxy carboxylate ester,
19) tristyrylphenol alkoxylate phosphate esters,
20) tristyrylphenol alkoxylate carboxylate esters,
21) phosphate esters of block copolymers of ethylene and propylene oxide and
22) alkylpolyglucosides.

* * * * *

UNITED STATES PATENT AND TRADEMARK OFFICE
CERTIFICATE OF CORRECTION

PATENT NO. : 6,232,272 B1
DATED : May 15, 2001
INVENTOR(S) : Johnnie R. Roberts et al It is certified that error appears in the above-identified patent and that said Letters Patent is hereby corrected as shown below:

<u>Column 5,</u>
Line 20, (claim 2, line 10), change " mercoprop" to -- mecoprop --.

Signed and Sealed this

Thirtieth Day of October, 2001

Attest:

*Nicholas P. Godici*

NICHOLAS P. GODICI
*Attesting Officer*     *Acting Director of the United States Patent and Trademark Office*